United States Patent [19]

Sih

[11] 4,271,292

[45] Jun. 2, 1981

[54] 2-DECARBOXY-2-TETRAZOLYL-19-KETO-PG COMPOUNDS

[75] Inventor: John C. Sih, Kalamazoo, Mich.

[73] Assignee: The Upjohn Company, Kalamazoo, Mich.

[21] Appl. No.: 132,225

[22] Filed: Mar. 20, 1980

Related U.S. Application Data

[62] Division of Ser. No. 25,879, Apr. 2, 1979, abandoned.

[51] Int. Cl.³ .................. C07C 177/00; C07D 257/06
[52] U.S. Cl. ...................................... 542/429; 548/253
[58] Field of Search ...................... 542/429; 548/253

[56] References Cited

U.S. PATENT DOCUMENTS

| | | | |
|---|---|---|---|
| 3,953,466 | 4/1976 | Hess et al. | 548/253 |
| 4,024,179 | 5/1977 | Bindra et al. | 548/253 |
| 4,152,527 | 5/1979 | Hess et al. | 548/253 |
| 4,177,346 | 12/1979 | Nelson | 548/253 |

OTHER PUBLICATIONS

Sih et al. (I) J. Am. Chem. Soc. 91 (1969) pp. 3605–3607.
Hayashi et al. Chem. Abst. 86 (1977) #43265.
Sih et al. Prostaglandins 13 (1977) pp. 832–835.

*Primary Examiner*—Arthur P. Demers
*Attorney, Agent, or Firm*—Robert A. Armitage

[57] ABSTRACT

The present invention provides novel 2-decarboxy-2-tetrazolyl-19-keto-PG compounds, which are useful for a variety of pharmacological purposes, e.g., antiasthmatic indications.

5 Claims, No Drawings

2-DECARBOXY-2-TETRAZOLYL-19-KETO-PG COMPOUNDS

DESCRIPTION

CROSS REFERENCE TO RELATED APPLICATION

This application is a division of Ser. No. 025,879, filed Apr. 2, 1979, now abandoned.

BACKGROUND OF THE INVENTION

The present invention relates to novel prostaglandin analogs. Particularly, the invention relates to prostaglandin analogs wherein the C-19 position is substituted by oxo, i.e., 19-keto-PG compounds or 19-oxo-PG compounds. Most particularly, the present invention relates to novel 2-decarboxy-2-tetrazolyl-19-keto-PG compounds, a disclosure of the preparation and pharmacological use of which is incorporated here by reference from U.S. Ser. No. 025,899, filed Apr. 2, 1979.

PRIOR ART

Prostaglandins exhibiting a variety of substitution at the C-19 position are known. See particularly J. C. Sih, et al., JACS 91:3685 (1969) wherein 19-oxo-PGE$_2$ and 13,14-dihydro-19-oxo-PGE$_1$ are disclosed. Further, Chemical Abstracts 86:43265H purportedly discloses 19-oxo-PGF$_2\alpha$. The abstract is derived from Japanese Kokai 76 82,245.

SUMMARY OF THE INVENTION

The present invention particularly provides:
a compound of the formula

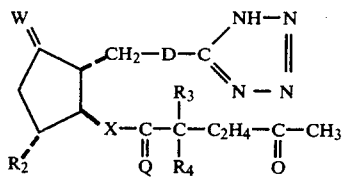

wherein D is
(1) cis—CH=CH—CH$_2$—(CH$_2$)$_g$—CH$_2$—,
(2) cis—CH=CH—CH$_2$—(CH$_2$)$_g$—CH$_2$—,
(3) cis—CH$_2$—CH=CH—CH$_2$—CH$_2$—,
(4) trans—(CH$_2$)$_3$—CH=CH—,
(5) —(CH$_2$)$_3$—(CH$_2$)$_g$—CH$_2$—,
(6) —(CH$_2$)$_3$—CH$_2$—CF$_2$—,
(7) —(CH$_2$)$_3$—O—CH$_2$—,
(8) —(CH$_2$)—O—(CH$_2$)$_2$—,
(9) —CH$_2$—O—(CH$_2$)$_3$—,
(10) —(m—Ph)—(CH$_2$)$_2$—, or
(11) —(m—Ph)—O—CH$_2$—,
wherein —(m—Ph)— is inter-meta-phenylene and
wherein g is zero, one, two, or three;
wherein Q is $\alpha$—OH:$\beta$—R$_5$ or $\alpha$—R$_5$:$\beta$—OH, wherein R$_5$ is hydrogen or methyl;
wherein R$_2$ is hydrogen, hydroxyl, or hydroxymethyl, wherein R$_3$ and R$_4$ are hydrogen, methyl, or fluoro, being the same or different, with the proviso that one of R$_3$ and R$_4$ is fluoro only when the other is hydrogen or fluoro; and
wherein W is oxo, methylene, $\alpha$—OH:$\beta$—H, or $\alpha$—H:$\beta$—OH; and
wherein X is cis- or trans—CH=CH—, —C≡C— or —CH$_2$CH$_2$—.

The compounds of the present invention are particularly useful for inducing prostaglandin-like biological effects, as described in U.S. Ser. No. 026,066. Uses of compounds in accordance with the present invention include, therefore, antiasthmatic indications.

DESCRIPTION OF THE PREFERRED EMBODIMENTS

The present invention particularly relates to:
2-decarboxy-2-tetrazolyl-19-keto-PGF$_2\alpha$.
I claim:

1. A compound of the formula

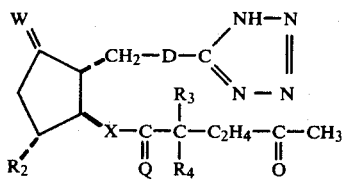

wherein D is
(1) cis—CH=CH—CH$_2$—(CH$_2$)$_g$—CH$_2$—,
(2) cis—CH=CH—CH$_2$—(CH$_2$)$_g$—CH$_2$—,
(3) cis—CH$_2$—CH=CH—CH$_2$—CH$_2$—,
(4) trans—(CH$_2$)$_3$—CH=CH—,
(5) —(CH$_2$)$_3$—(CH$_2$)$_g$—CH$_2$—,
(6) —(CH$_2$)$_3$—CH$_2$—CF$_2$—,
(7) —(CH$_2$)$_3$—O—CH$_2$—,
(8) —(CH$_2$)—O—(CH$_2$)$_2$—,
(9) —CH$_2$—O—(CH$_2$)$_3$—,
(10) —(m-Ph)—(CH$_2$)$_2$—, or
(11) —(m-Ph)—O—CH$_2$—,
wherein —(m-Ph)— is inter-meta-phenylene and
wherein g is zero, one, two, or three;
wherein Q is $\alpha$—OH:$\beta$—R$_5$ or $\alpha$—R$_5$:$\beta$—OH, wherein R$_5$ is hydrogen or methyl;
wherein R$_2$ is hydrogen, hydroxyl, or hydroxymethyl, wherein R$_3$ and R$_4$ are hydrogen, methyl, or fluoro, being the same or different, with the proviso that one of R$_3$ and R$_4$ is fluoro only when the other is hydrogen or fluoro; and
wherein W is oxo, methylene, $\alpha$—OH:$\beta$—H, or $\alpha$—H:$\beta$—OH; and
wherein X is cis- or trans—CH=CH—, —C≡C— or —CH$_2$CH$_2$—.

2. A compound according to claim 1, wherein D is cis-CH=CH—CH$_2$—(CH$_2$)$_g$—CH$_2$—.

3. A compound according to claim 2, wherein W is $\alpha$—OH:$\beta$—H.

4. A compound according to claim 3, wherein R$_2$ is hydroxyl and X is trans-CH=CH—.

5. 2-Decarboxy-2-tetrazolyl-19-keto-PGF$_2\alpha$, a compound according to claim 4.

* * * * *

UNITED STATES PATENT OFFICE
CERTIFICATE OF CORRECTION

Patent No. 4,271,292  Dated 2 June 1981

Inventor(s) John C. Sih

It is certified that error appears in the above-identified patent and that said Letters Patent are hereby corrected as shown below:

Column 1, line 46, and Column 2, line 31,

"cis-$CH=CH-CH_2-(CH_2)g-CH_2-$" should read -- cis-$CH=CH-CH_2-(CH_2)g-CF_2-$ --.

Signed and Sealed this

Twenty-second Day of December 1981

|SEAL|

*Attest:*

*Attesting Officer*

GERALD J. MOSSINGHOFF

*Commissioner of Patents and Trademarks*